United States Patent [19]
Cole et al.

[11] Patent Number: 5,872,271
[45] Date of Patent: Feb. 16, 1999

[54] **ENDOGENOUS VEGETABLE OIL DERIVED FROM *HELIANTHUS ANNUUS* SEEDS WHEREIN THE LEVELS OF PALMITIC ACID AND OLEIC ACID ARE PROVIDED IN AN ATYPICAL COMBINATION**

[75] Inventors: Glenn S. Cole, Woodland, Calif.; Jan P. Hazebroek, Johnston, Iowa; Thomas C. Heaton, Davis, Calif.

[73] Assignee: Pioneer Hi-Bred International, Inc., Johnston, Iowa

[21] Appl. No.: 933,357

[22] Filed: Sep. 18, 1997

Related U.S. Application Data

[62] Division of Ser. No. 475,974, Jun. 7, 1995, Pat. No. 5,710,366.

[51] Int. Cl.$^6$ .................................................. C07C 57/00
[52] U.S. Cl. ..................... 554/223; 426/601; 426/607; 424/195.1
[58] Field of Search ................................... 554/223, 601, 554/607, 195.1

[56] References Cited

U.S. PATENT DOCUMENTS

| | | | |
|---|---|---|---|
| 4,297,292 | 10/1981 | Logan et al. | 554/87 |
| 4,627,192 | 12/1986 | Fick | 47/58 |
| 4,743,402 | 5/1988 | Fick | 554/223 |
| 5,276,264 | 1/1994 | Heaton et al. | 800/200 |
| 5,387,758 | 2/1995 | Wong et al. | 800/230 |

OTHER PUBLICATIONS

Dobarganes et al., "Thermal Stability and Frying Performance of Genetically Modified Sunflower Seed (Helianthus annuus L.) Oils", Agric Food Chem. 1993, vol. 41, No. 4, pp. 678–681.

Fernandez–Martinez et al., "Genetic Analysis of the High Oleic Acid Content in Cultivated Sunflower (Helianthus annuus L.)", Euphytica, 1989, vol. 41, pp. 39–51.

Garces et al., "Oleate Desaturation in Seeds of Two Genotypes of Sunflower", Phytochemistry, 1989, vol. 28. No. 10, pp. 2593–2595.

Garces et al., "Lipid Characterization in Seeds of a High Oleic Acid Sunflower Mutant", Phytochemistry, 1989, vol. 28, No. 10, pp. 2597–2600.

Kharchenko, "Genotypic and Phenotypic Mechanisms Ensuring Regulation of Fatty Acid Biosynthesis in Sunflower Seed", Soviet Plant Physiology, 1979, vol. 26, pp. 933–998.

Miller et al., "ND–01, a High Oleic Acid Sunflower Synthetic", North Dakota Farm Research, 1984, vol. 42, pp. 27–32.

Vick et al., "Release of ND–01, a High Oleic Acid Sunflower Synthetic", Proceedings Sunflower Research Workshop, Feb. 1, 1984. pp. 8–9.

"Achievements of Sunflower Breeding in the USSR", A.V. Pukhalsky et al., *Proc. 8th Int. Sunflower Conf.*, pp. 48 to 55 (1978).

"Sunflower Breeding for High Palmitic Acid Content in Oil", Peter Ivonov et al., *Proc. 12th Int. Sunflower Conf.*, pp. 463–465 (1988).

"Sunflower Mutants with Altered Fatty Acid Composition in Seed Oil" by Rafael Garcés et al., *Plant Lipid Metabolism*, pp.512 to 514 (1995).

"Mutant Sunflowers with High Concentration of Saturated Fatty Acids in the Oil", by J. Osorio et al., *Crop Science*, vol. 35, pp. 739 to 742 (1995).

"Inheritance of High Oleic Acid in Sunflower", Urie, *Crop Science*, vol. 25, pp. 986 to 989 (1985).

"Correlations of Oil Content and Fatty Acid Composition in Hlgh Oleic Lines and Hybrids of Sunflower" (H. Annus L.), Petakov et al., *Biotechnal & Biotechnal Eq.*, vol. 7 (4), pp. 136 to 138 (1993).

*Primary Examiner*—Samuel Barts
*Assistant Examiner*—Deborah D Carr
*Attorney, Agent, or Firm*—Burns, Doane, Swecker & Mathis, L.L.P.

[57] ABSTRACT

Sunflower plants, seeds capable of forming the same, and a novel endogenous vegetable oil derived from such sunflower seeds are provided. The plants have the ability to yield an endogenous vegetable oil wherein the levels of palmitic acid and oleic acid are provided in an atypical combination via genetic control. The concentration of palmitic acid in the endogenous oil constitutes at least 20 (e.g., approximately 20 to 45) percent by weight of the total fatty acid content, and the concentration of oleic acid in the oil constitutes at least 45 (e.g., approximately 45 to 65) percent by weight of the total fatty acid content in the absence of hydrogenation or other chemical or physical modification. It was found that the plants of the present invention can be formed through the combination (as described) of genetic determinants that were found to be present in the Pervenets sunflower and the H-55-9-2-1 or H-55-9-2-2 sunflower. The novel endogenous oil of the present invention is particularly useful, inter alia, in the production of margarine, or a cocoa butter equivalent.

15 Claims, No Drawings

ENDOGENOUS VEGETABLE OIL DERIVED FROM *HELIANTHUS ANNUUS* SEEDS WHEREIN THE LEVELS OF PALMITIC ACID AND OLEIC ACID ARE PROVIDED IN AN ATYPICAL COMBINATION

This application is a divisional, of Application No. 08/475,974, filed Jun. 7, 1995 now U.S. Pat. No. 5,770,366.

BACKGROUND OF THE INVENTION

Sunflowers (i.e., *Helianthus annuus*) are being grown as an increasingly important oilseed crop in many parts of the world. The cultivated sunflower is a major worldwide source of vegetable oil. In the United States, approximately 2 to 3 million acres are planted in sunflowers annually, primarily in the Dakotas and Minnesota. It is recognized that commonly available sunflower plants typically form an endogenous oil within their seeds that primarily includes the following fatty acids in the stated concentrations by weight based upon the total fatty acid content:

| Fatty Acid | Chemical Structure | Approximate Concentration (weight percent) |
|---|---|---|
| Palmitic | C16:0 | 7 |
| Palmitoleic | C16:1 | .01 |
| Stearic | C18:0 | 4 |
| Oleic | C18:1 | 17 to 20 |
| Linoleic | C18:2 | 69 to 72. |

See in this regard Table 3 found at Page 409 of *Sunflower Science and Technology*, Edited by Jack F. Carter (1978). Accordingly, the quantity of pahmitic acid (C16:0) commonly present in the endogenous sunflower oil has been relatively low and the quantity of the polyunsaturated linoleic acid (C18:2) found in the endogenous sunflower oil commonly has been relatively high.

Research conducted in the Soviet Union has reported the development, through chemical mutagenesis, of the Pervenets sunflower from which concentrations of oleic acid (C18:1) in the oil as high as 89.5 percent by weight based upon the total fatty acid content have been reported. See, for instance, "Achievements of Sunflower Breeding in the USSR", by A. V. Pukhalsky et al., *Proc. 8th Int. Sunflower Conf.*, Pages 48 to 55 (1978). Plant material from this research has been made available to the public and forms the basis for the high oleic acid sunflower varieties that are available today. See also, U.S. Pat. Nos. 4,627,192 and 4,743,402 for a further discussion of the high oleic acid characteristic in the sunflower plant. A sunflower wherein the endogenous levels of both palmitic acid (C16:0) and oleic acid (C18:1) are provided in an atypical combination of relatively high concentrations is not provided by such research.

Sunflower mutagenesis research conducted in Bulgaria is reported to have yielded an endogenous sunflower oil wherein the concentration of palmitic acid (C16:0) is significantly increased to levels which averaged 40.2 percent by weight in at least some instances. However, in all instances the concentration of the polyunsaturated linoleic acid (C18:2) remained high and substantially exceeded that of the oleic acid (C18:1) that concomitantly was present. See, "Sunflower Breeding for High Palmitic Acid Content in the Oil" by Peter Ivonov et al., *Proc. 12th Int. Sunflower Conf.*, Pages 463 to 465 (1988). A sunflower plant wherein the endogenous levels of both palmitic acid (C16:0) and oleic acid (C18:1) are provided in an atypical combination of relatively high concentrations is not provided by such research.

Further sunflower mutagenesis research conducted in Spain in an effort to make changes in the distribution of fatty acids in the endogenous vegetable oil has been recently reported in the published literature. See, (1) "Sunflower Mutants With Altered Fatty Acid Composition in the Seed Oil" by Rafael Garces et al., *Plant Lipid Metabolism*, Pages 512 to 514 (1995), and (2) "Mutant Sunflowers with High Concentration of Saturated Fatty Acids in the Oil" by J. Osorio et al., *Crop Science*, Vol. 35, Pages 739 to 742 (1995). Such research indicates an elevation in the palmitic acid (C16:0) concentration while continuing to produce a significant concentration of linoleic acid (C18:2). Such publications were issued after the completion of the present invention, and do not disclose the presently claimed contribution. Also, these disclosures are believed to be non-enabling since the different plant material resulting from such mutagenesis research is not believed to be available to the public.

It is an object of the present invention to provide novel sunflower plants that form seeds which contain an endogenous oil wherein the levels of palmitic acid (C16:0) and oleic acid (C18:1) are provided in an atypical combination via genetic control.

It is an object of the present invention to provide novel sunflower seeds which contain an endogenous oil wherein the levels of palmitic acid (C16:0) and oleic acid (C18:1) are provided in an atypical combination via genetic control.

It is an object of the present invention to provide a novel endogenous sunflower oil which exhibits in the absence of hydrogenation or other chemical or physical modification an atypical combination of concentrations of palmitic acid (C1 6:0) and oleic acid (C18:1) that is under genetic control.

It is an object of the present invention to provide novel sunflower plants that form seeds which contain an endogenous oil wherein an atypical combination of levels of palmitic acid (C16:0) and oleic acid (C18:1) is formed under conventional sunflower field growing conditions while under genetic control.

It is an object of the present invention to provide a novel endogenous sunflower oil that is suitable for use in the production of margarine, shortening, a cocoa butter equivalent, etc. without the requirement of substantial hydrogenation.

It is another object of the present invention to provide an endogenous sunflower oil that exhibits a smooth mouth feel in view of the presence of a high concentration of palmitic acid (C16:0) coupled with the stability attributable to a relatively high concentration of the monounsaturated oleic acid (C18:1) and a low concentration of polyunsaturated linoleic acid (C18:2).

It is a further object of the present invention to provide a process for the formation of sunflower seeds wherein the levels of palmitic acid (C16:0) and oleic acid (C18:1) are provided in an atypical advantageous combination.

These and other objects and advantages of the invention will be apparent to those skilled in the art from the following description and appended claims.

SUMMARY OF THE INVENTION

An endogenous vegetable oil derived from *Helianthus annuus* seeds is provided which exhibits in the absence of hydrogenation or other chemical or physical modification (1) at least 20 percent by weight of palmitic acid based upon the total fatty acid content, and (2) at least 45 percent by weight of oleic acid based upon the total fatty acid content, which oil was extracted from seeds possessing genetic means for the expression of the stated fatty acids in the stated concentrations.

A mature *Helianthus annuus* oilseed is provided which bears an endogenous oil wherein the levels of palmitic acid and oleic acid are provided in an atypical combination via genetic control, the oilseed bearing an oil which exhibits following crushing and extraction in the absence of hydrogenation or other chemical or physical modification (1) at least 20 percent by weight of palmitic acid based upon the total fatty acid content, and (2) at least 45 percent by weight of oleic acid based upon the total fatty acid content.

An oilseed *Helianthus annuus* plant is provided which is capable of forming oilseeds that yield an endogenous oil wherein the levels of palmitic acid and oleic acid are provided in an atypical combination of concentrations via genetic control wherein the oil exhibits following crushing and extraction in the absence of hydrogenation or other chemical or physical modification (1) at least 20 percent by weight of palmitic acid based upon the total fatty acid content, and (2) at least 45 percent by weight of oleic acid based upon the total fatty acid content.

A process is provided for the formation of *Helianthus annuus* plants capable of forming oilseeds that yield an endogenous oil wherein the levels of palmitic acid and oleic acid are provided in an atypical combination of concentrations in the absence of hydrogenation or other chemical or physical modification that comprises:

(a) crossing a sunflower plant that has a lineage which includes the Pervenets sunflower with a sunflower plant that has a lineage which includes the H-55-9-2-1 or H-55-9-2-2 sunflower, (b) self-pollinating $F_1$ progeny plants of step (a) for at least two generations to produce inbred plants, (c) selecting from the progeny of step (b) a plant that exhibits in the endogenous oil formed in the oilseeds thereof a combination of at least 20 percent by weight of palmitic acid based upon the total fatty acid content and at least 45 percent by weight of oleic acid based upon the total fatty acid content wherein the levels of palmitic acid and oleic acid are under genetic control, and (d) forming plants that include the selection of step (c) in their lineage that continue to exhibit an endogenous oil formed in the oilseeds thereof a combination of at least 20 percent by weight of palmitic acid based upon the total fatty acid content and at least 45 percent by weight of oleic acid based upon the total fatty acid content wherein the levels of palmitic acid and oleic acid continue to be under genetic control.

DESCRIPTION OF PREFERRED EMBODIMENTS

It has been found that the sunflower plants of the present invention can be created through the combination of sunflower genetic determinants that heretofore were not recognized to make possible the formation of a novel endogenous oil wherein the levels of palmitic acid (C16:0) and oleic acid (C18:1) are provided in an atypical combination via genetic control.

The first essential parental sunflower plant is the Pervenets sunflower including any sunflower that is derived directly or indirectly therefrom (i.e., any sunflower that includes the Pervenets sunflower in its lineage). As previously indicated, Pervenets was developed in the Soviet Union, and sunflower seed of Pervenets and numerous varieties derived therefrom is well known to sunflower plant breeders and is publicly available from a number of sources throughout the world including (1) the U.S. Department of Agriculture Crop Science Lab, Seedstocks Project, North Dakota State University, Fargo, N.Dak., U.S.A., (2) the U.S. Department of Agriculture Plant Introduction Station, Ames, Iowa, U.S.A., and (3) INIA of Cordoba, Spain. Pervenets is available from the U.S. Department of Agriculture Plant Introduction Station as PI483077. Representative publicly-available sunflower varieties and sources for their acquisition that were derived from Pervenets and accordingly are suitable for utilization as parental sunflower plants in accordance with the present invention include: HA341, HA342, HA343, HA349, HA350, HA351, HA352, HA353, RHA344, RHA345, RHA346, RHA347, RHA348, RHA354, RHA355, and populations ND-01 and ND-02 from the U.S. Department of Agriculture, and R-OL-71 and HA-OL-9 from INIA of Cordoba, Spain. Pervenets and these representative sunflower varieties have the ability to form an elevated level of oleic acid (C18:1) in the endogenous oil that commonly is at least 80 percent by weight based upon the total fatty acid content wherein the production of oleic acid is under genetic control. Such parental plants are recognized to form an endogenous vegetable oil that includes a somewhat typical concentration of palmitic acid (C16:0) that commonly constitutes approximately 2.5 to 6.0 percent by weight and a palmitoleic fatty acid (C16:1) content of approximately 0.1 to 0.5 percent by weight based upon the total fatty acid content. Best results are achieved when a parental plant is selected that exhibits good agronomic characteristics in the area where the resulting sunflower plant of the present invention is to be grown.

The second essential parental sunflower plant is the H-55-9-2-1 or H-55-9-2-2 sunflower including any sunflower that is derived directly or indirectly therefrom (ie., any sunflower that includes H-55-9-2-1 or H-55-9-2-2 in its lineage). These sunflower plants were created by Dr. Willem Vermeulen as maintainer varieties and were released to the public beginning in January, 1978 by the Oil & Protein Seed Centre, Grain Crops Institute, Agricultural Research Council, located at Potchefstroom, Republic of South Africa. It is understood that H-55-9-2-1 and H-55-9-2-2 include a Romanian germplasm in their backgrounds. H-55-9-2-1 and H-55-9-2-2 and sunflower varieties derived therefrom have the ability to form an endogenous sunflower oil that forms somewhat typical levels of palmitic acid (C16:0) of approximately 4.5 to 6.0 percent by weight, palmitoleic acid (C16:1) of approximately 0.1 to 0.5 percent by weight, oleic acid (C18:1) of approximately 16 to 26 percent by weight, and linoleic acid (C18:2) of approximately 63 to 72 percent by weight each based upon the total fatty acid content. Best results are achieved when a parental plant is selected that exhibits good agronomic characteristics in the area where the resulting sunflower plant of the present invention is to be grown.

In accordance with the process of the present invention a sunflower plant that has a lineage which includes the Pervenets sunflower is crossed under controlled conditions with a sunflower plant that has a lineage which includes H-55-9-2-1 or H-55-9-2-2 to produce progeny plants. Such progeny plants form the $F_1$ cross are self-pollinated for at least two generations (e.g., 2 to 6, or more generations) to produce inbred plants.

A selection is made from the resulting inbred plants that exhibits an endogenous oil formed in the oilseeds thereof having a combination of at least 20 (e.g., approximately 20 to 45) percent by weight of palmitic acid (C16:0) based upon the total fatty acid content and at least 45 (e.g., approximately 45 to 65) percent by weight of oleic acid (C18:1) based upon the total fatty acid content wherein the levels of palmitic acid (C16:0) and oleic acid (C18:1) are under genetic control. The concentration of palmitic acid (C16:0) in the endogenous oil preferably is at least 25 percent by weight based upon the total fatty acid content, and most preferably is at least 30 percent by weight (e.g., at least 35 percent by weight) based upon the total fatty acid content. The endogenous oil obtained from the selection in a preferred embodiment additionally contains at least 4 (e.g., approximately 4 to 15) percent by weight of palmitoleic acid (C16:1) and no more than 10 (e.g., 1 to 10) percent by weight of linoleic acid (C18:2) based upon the total fatty acid content. In another preferred embodiment the combined concentration of palmitic acid (C16:0) and palmitoleic acid (C16:1) is at least 40 (e.g., approximately 40 to 45 or more) percent by weight based upon the total fatty acid content. In a further preferred embodiment of the process of the present invention, the selection of an inbred for the stated concentration of palmitic acid (C16:0), and optionally also palmitoleic acid (C16:1), initially is carried out, and the selection for the stated concentration of oleic acid (C18:1) is carried out in a subsequent generation following further inbreeding while continuing to exhibit the specified concentration of palmitic acid (C16:0). The selection process can be expedited through the analysis of halfseeds while carefully preserving the remaining halfseed intact for the creation of a new plant wherein the same requisite endogenous fatty acid profile is observed. The formation of each of the recited fatty acids in the specified concentration is under genetic control. Plants in accordance with the present invention reliably can be formed under conventional sunflower field growing conditions.

Each of the above-identified concentrations of the specified fatty acids in the endogenous sunflower oil obtained by simple crushing and extraction in the absence of hydrogenation or other chemical or physical modification is under genetic control as can be confirmed by examination of progeny for the specified characteristics. The genetic means for the expression of the recited traits can also be transferred by standard plant breeding to other sunflower plants where the same atypical combination of concentrations of fatty acids is exhibited.

The formation of an endogenous sunflower vegetable oil containing at least 20 percent by weight of palmitic acid (C16:0) in a background of relatively high oleic acid (C18:1) is considered to be surprising and is incapable of simple explanation since this trait was not publicly available in the past and was not expressed by either of the initial parental plants. It is believed in view of the results herein reported that the expression of this level of palmitic acid in a relatively high oleic acid (C18:1) background is the result of the homozygous presence of recessive genes for this palmitic acid (C16:0) trait in combination with the requisite level of somewhat complex modifier genes wherein both parental plants contribute to the overall genetic complement that is essential. A novel endogenous sunflower vegetable oil thereby is provided.

In order to make a determination of the fatty acids present in the endogenous sunflower oil and their respective concentrations, mature sunflower seeds are crushed (e.g., in a hydraulic press), and the endogenous oil can be readily extracted with hexane or by other suitable techniques in accordance with procedures known in the art. Following transmethylation, the methyl esters of the fatty acids are separated and their concentrations can be determined by use of capillary gas chromatography in accordance with standard operating procedures. For instance, one can utilize a Hewlett-Packard 5890 gas chromatograph and a 7673 autosampler with a flame ionization detector. The data can be collected and integrated using Perkin Elmer software in conjunction with Perkin Elmer interfaces. The integrated areas of the peaks corresponding to the methyl esters of the various fatty acids are grouped and are normalized to yield their relative abundances. See "Automating Fatty Acid Analyses From Seeds" by Thomas B. Brumback, Jr. et al., *Chemiometrics and Intelligent Laboratory Systems: Laboratory Information Management*, Vol. 21, Page 215 to 222 (1993). Other analytical techniques similarly can be utilized that are known to yield reliable results, such as the American Oil Chemists Society (AOCS) Official Method Ce 1e-91.

The sunflower plants of the present invention preferably are provided as a substantially homogeneous stand. The sunflower seeds of the present invention preferably are provided in a substantially homogeneous assemblage. The endogenous vegetable oil of the present invention preferably is provided in a quantity of at least one liter. Also, the endogenous vegetable oil contains a substantial concentration of the Beta' triglyceride crystal structure wherein the oleic acid component is present at the second or middle position of the triglyceride.

The genetic means for the expression of the recited levels of fatty acids in the endogenous vegetable oil once established reliably can be transferred to other sunflower plants via conventional plant breeding wherein plants are formed and are selected that continue to exhibit such recited combination of fatty acid levels. The genetic determinants for such fatty acid profile preferably is introduced into inbred varieties that exhibit highly satisfactory agronomic characteristics or into both parental plants that when combined while using conventional plant breeding techniques form $F_1$ sunflower varieties that are agronomically well adapted for the intended growing site. Additional satisfactory maintainer lines can be formed by crossing into known maintainer lines, open-pollinated varieties, or wild species accessions. Satisfactory cytoplasmically male sterile lines can be formed by backcrossing into known cytoplasmically male sterile lines. Satisfactory restorer lines can be formed by crossing into known restorer lines, commercial hybrids, open-pollinated varieties, or wild species accessions. For best results during $F_1$ hybrid production significant genetic diversity is provided between the cytoplasmically male sterile plants and the restorer plants so as to promote yield advantages in the resulting hybrid via heterosis.

A highly attractive vegetable oil of non-tropical origin is provided that commonly is a liquid at room temperature. The unique levels of fatty acids provided in the endogenous sunflower oil of the present invention make possible a number of end uses wherein such concentrations of the fatty acids can serve to advantage. For instance, such vegetable oil with only minimal hydrogenation can be used in the production of margarine (e.g., a tub margarine), shortening, a cocoa butter equivalent, etc. Such relatively low level of hydrogenation which can be partial or substantially complete leads to a relatively low level of trans-fatty acids in the resulting product. Alternatively, the resulting oil can be utilized as a blending oil in the production of various lotions for application to the skin, or in other food products such as peanut butter, pastry, or confectionery. The relatively high concentration palmitic acid (C16:0) promotes a smooth mouth feel. Also, any palmitoleic acid (C16:1) that is present readily can also be converted to palmitic acid (C16:0) upon hydrogenation. The relatively low level of polyunsaturated linoleic acid (C18:2) present in the endogenous oil of the present invention leads to enhanced stability. As previously indicated, linoleic acid (C18:2) commonly is present in conventional sunflower oil as the primary component.

The following Examples are presented as a specific illustrations of the claimed invention. It should be understood, however, that the invention is not limited to the specific details set forth in the Examples.

EXAMPLE I

An inbred selection of Pervenets was utilized as the male parent and was crossed under controlled conditions with H-55-9-2-2 as the female parent. The male parent derived from Pervenets exhibited an endogenous oil in its seeds of approximately 4.0 percent by weight palmitic acid (C16:0), approximately 0.1 percent by weight of palmitoleic acid (C16:1), approximately 89.0 percent by weight of oleic acid (C18:1), and approximately 2.0 percent by weight of linoleic acid (C18:2) with all percentages being based upon the total fatty acid content. The H-55-9-2-2 parent exhibited an endogenous oil in its seeds of approximately 5.0 percent by weight palmitic acid (C16:0), approximately 0.1 percent by weight of palmitoleic acid (C16:1), approximately 22.0 percent by weight of oleic acid (C18:1), and approximately 67.0 percent by weight of linoleic acid (C18:2) with all percentages being based upon the total fatty acid content. When the endogenous oils of a number of the resulting $F_1$ plants were analyzed, they were found in all instances to exhibit a somewhat conventional palmitic acid (C16:0) concentration of approximately 7.0 percent by weight, a palmitoleic acid (C16:1) concentration of approximately 0.3 percent by weight, an oleic acid (C18:1) concentration of approximately 40.0 percent by weight, and a linoleic acid (C18:2) concentration of approximately 40.0 percent by weight, with each being based upon the total fatty acid content. An $F_1$ plant designated H-55-9-2-2/Pervenets was self-pollinated for six generations and the endogenous oil formed in a single seed surprisingly was found via half-seed analysis to exhibit a palmitic acid (C16:0) concentration of 25.4 percent by weight, a palmitoleic acid (C16:1) concentration of 8.1 percent by weight, an oleic acid (C18:1) concentration of 62.6 percent by weight, and a linoleic acid (C18:2) concentration of 1.6 percent by weight, with each based upon the total fatty acid content.

A plant produced from the remaining half-seed was produced and was self-pollinated for 2 generations to produce a maintainer inbred designated 93PMOL040G. Bulked seed from a single head was planted in an isolation cage with bees and a bulk of the seeds from all the cross-pollinated heads was made. An analysis of 10 grams of whole seeds of 93PMOL040G using American Oil Chemists Society (AOCS) Official Method Ce 1e-91 has determined that a fatty acid distribution is exhibited within the endogenous vegetable oil as reported in Table A based upon the total fatty acid content following grinding and Soxhlet extraction in the absence of hydrogenation or other chemical or physical modification.

TABLE A

| Fatty Acid | Number of Carbon Atoms Per Molecule | Number of Double Bonds Per Molecule | Weight Percent of Oil of 93PMOL040G |
| --- | --- | --- | --- |
| Lauric | 12 | 0 | <0.1 |
| Myristic | 14 | 0 | <0.1 |
| Palmitic | 16 | 0 | 23.2 |
| Palmitoleic | 16 | 1 | 5.4 |
| Stearic | 18 | 0 | 2.9 |
| Oleic | 18 | 1 | 61.1 |
| Linoleic | 18 | 2 | 4.0 |
| Alpha-linolenic | 18 | 3 | 0.1 |
| Arachidic | 20 | 0 | 0.5 |

TABLE A-continued

| Fatty Acid | Number of Carbon Atoms Per Molecule | Number of Double Bonds Per Molecule | Weight Percent of Oil of 93PMOL040G |
| --- | --- | --- | --- |
| Eicosenoic | 20 | 1 | 0.2 |
| Behenic | 22 | 0 | 1.8 |
| Erucic | 22 | 1 | <0.01 |
| Lignoceric | 24 | 0 | 0.6 |

Sunflower seeds of 93PMOL040G have been deposited under the Budapest Treaty at the American Type Culture Collection, 12301 Parklawn Drive, Rockville, Md. 20852, U.S.A., under Accession No. 97159.

Cytoplasmically male sterile plants for use with 93PMOL040G in the production of an $F_1$ hybrid variety in accordance with the present invention were produced by backcrossing 93PMOL040G for 6 generations with a cytoplasmically male sterile sunflower possessing a high concentration of oleic acid in the endogenous oil. The resulting cytoplasmically male sterile plants have been designed 93PMOL040F. An analysis of 10 grams of whole seeds of 93PMOL040F using American Oil Chemists Society (AOCS) Official Method Ce 1e-91 has determined that a fatty acid distribution is exhibited within the endogenous vegetable oil as reported in Table B based upon the total fatty acid content following grinding and Soxhlet extraction in the absence of hydrogenation or other chemical or physical modification.

TABLE B

| Fatty Acid | Number of Carbon Atoms Per Molecule | Number of Double Bonds Per Molecule | Weight Percent of Oil of 93PMOL040F |
| --- | --- | --- | --- |
| Lauric | 12 | 0 | <0.1 |
| Myristic | 14 | 0 | <0.1 |
| Palmitic | 16 | 0 | 21.4 |
| Palmitoleic | 16 | 1 | 4.4 |
| Stearic | 18 | 0 | 3.2 |
| Oleic | 18 | 1 | 61.9 |
| Linoleic | 18 | 2 | 6.0 |
| Alpha-linolenic | 18 | 3 | 0.1 |
| Arachidic | 20 | 0 | 0.5 |
| Eicosenoic | 20 | 1 | 0.2 |
| Behenic | 22 | 0 | 1.6 |
| Erucic | 22 | 1 | <0.01 |
| Lignoceric | 24 | 0 | 0.5 |

Sunflower seeds of 93PMOL040F have been deposited under the Budapest Treaty at the American Type Culture Collection, 12301 Parklawn Drive, Rockville, Md. 20852, U.S.A. under Accession No. 97158.

Suitable restorer plants for 93PMOL040F can be produced by crossing known restorer lines with 93PMOL040F, and subsequently selfing-out such restorer plants. When 93PMOL040F is crossed with the resulting restorer plant, the resulting progeny will continue to exhibit an endogenous vegetable oil in accordance with the present invention wherein the respective levels of fatty acids are under genetic control.

Sunflower seeds containing higher levels of palmitic acid (C16:0) and palmitoleic acid (C16:1) within the endogenous vegetable oil than reported in Table A and in Table B while under genetic control can be selected from among the seeds of 93PMOL040G and 93PMOL040F. For instance, palmitic acid (C16:0) concentrations exceeding 40 percent by weight and palmitoleic acid (C1 6:1) concentrations exceeding 10 percent by weight based upon the total fatty acid content have been observed.

EXAMPLE II

Example I can be repeated while substituting H-55-9-2-1 for H-55-9-2-2 and sunflower plants are provided which contain an endogenous oil within the seeds thereof wherein the levels of palmitic acid (C16:0) and oleic acid (C18:1) are present in an atypical combination while under genetic control.

Although the invention has been described with preferred embodiments, it is to be understood that variations and modifications may be resorted to as will be apparent to those skilled in the art. Such variations and modifications are to be considered within the purview and scope of the claims appended hereto.

We claim:

1. An endogenous vegetable oil derived from *Helianthus annuus* seeds which exhibits in the absence of hydrogenation or other chemical or physical modification (1) at least 20 percent by weight of palmitic acid based upon the total fatty acid content, and (2) at least 45 percent by weight of oleic acid based upon the total fatty acid content, which oil was extracted from seeds possessing genetic means for the expression of the stated fatty acids in the stated concentrations.

2. An endogenous vegetable oil derived from *Helianthus annuus* seeds according to claim 1 wherein said palmitic acid is present in a concentration of at least 25 percent by weight based upon the total fatty acid content.

3. An endogenous vegetable oil derived from *Helianthus annuus* seeds according to claim 1 wherein said palmitic acid is present in a concentration of at least 30 percent by weight based upon the total fatty acid content.

4. An endogenous vegetable oil derived from *Helianthus annuus* seeds according to claim 1 wherein said palmitic acid is present in a concentration of approximately 20 to 45 percent by weight based upon the total fatty acid content, and said oleic acid is present in a concentration of approximately 45 to 65 percent by weight based upon the total fatty acid content.

5. An endogenous vegetable oil derived from *Helianthus annuus* seeds according to claim 1 wherein palmitoleic acid additionally is present therein in a concentration of at least 4 percent by weight based upon the total fatty acid content.

6. An endogenous vegetable oil derived from *Helianthus annuus* seeds according to claim 1 wherein linoleic acid additionally is present therein in a concentration of no more than 10 percent by weight based upon the total fatty acid content.

7. An endogenous vegetable oil derived from *Helianthus annuus* seeds according to claim 1 wherein palmitoleic acid additionally is present therein in a concentration of at least 4 percent by weight based upon the total fatty acid content and linoleic acid additionally is present therein in a concentration of no more than 10 percent by weight based upon the total fatty acid content.

8. An endogenous vegetable oil derived from *Helianthus annuus* seeds according to claim 1 that was formed under conventional sunflower field growing conditions.

9. An endogenous vegetable oil derived from *Helianthus annuus* seeds according to claim 1 wherein said genetic means for the expression of the stated fatty acids in the stated concentrations is obtainable from 93PMOL040G.

10. An endogenous vegetable oil derived from *Helianthus annuus* seeds which exhibits in the absence of hydrogenation or other chemical or physical modification (1) approximately 20 to 45 percent by weight of palmitic acid based upon the total fatty acid content, (2) approximately 4 to 15 percent by weight of palmitoleic acid based upon the total fatty acid content, (3) approximately 45 to 65 percent by weight of oleic acid based upon the total fatty acid content, and (4) approximately 1 to 10 percent by weight of linoleic acid based upon the total fatty acid content, which oil was extracted from seeds possessing genetic means for the expression of the stated fatty acids in the stated concentrations.

11. An endogenous vegetable oil derived from *Helianthus annuus* seeds according to claim 10 wherein said palmitic acid is present in a concentration of at least 25 percent by weight based upon the total fatty acid content.

12. An endogenous vegetable oil derived from *Helianthus annuus* seeds according to claim 10 wherein said palmitic acid is present in a concentration of at least 30 percent by weight based upon the total fatty acid content.

13. An endogenous vegetable oil derived from *Helianthus annuus* seeds according to claim 10 that was formed under conventional sunflower field growing conditions.

14. An endogenous vegetable oil derived from *Helianthus annuus* seeds according to claim 10 wherein said genetic means for the expression of the stated fatty acids in the stated concentrations is obtainable from 93PMOL040G.

15. An endogenous vegetable oil derived from *Helianthus annuus* seeds according to claim 10 that is present in a quantity of at least one liter.

* * * * *